United States Patent [19]

McDonald

[11] Patent Number: 5,203,790
[45] Date of Patent: Apr. 20, 1993

[54] FOLDABLE PLASTIC OPTICAL LENS WITH REDUCED THICKNESS LIGHT BLOCKING SEGMENTS, AND ANCHORING MEANS

[75] Inventor: Henry H. McDonald, 65 N. Madison, #810, Pasadena, Calif. 91101

[73] Assignees: Henry H. McDonald; William W. Haefliger, both of Pasadena, Calif.

[21] Appl. No.: 807,204

[22] Filed: Dec. 16, 1991

Related U.S. Application Data

[63] Continuation-in-part of Ser. No. 791,002, Nov. 12, 1991.

[51] Int. Cl.$^5$ .............................................. A61F 2/16
[52] U.S. Cl. ........................................................ 623/6
[58] Field of Search ............................................. 623/6

[56] References Cited

U.S. PATENT DOCUMENTS

| | | | |
|---|---|---|---|
| 4,441,217 | 4/1984 | Cozean, Jr. | 623/6 |
| 4,573,998 | 3/1986 | Mazzocco | 623/6 |
| 4,605,409 | 8/1986 | Kelman | 623/6 |
| 4,731,078 | 3/1988 | Stoy et al. | 623/6 |
| 4,786,445 | 11/1988 | Portnoy et al. | 623/6 |
| 4,813,957 | 3/1989 | McDonald | 623/6 |
| 4,834,751 | 5/1989 | Knight et al. | 623/6 |
| 4,840,627 | 6/1989 | Blumenthal | 623/6 |
| 4,842,602 | 6/1989 | Nguyen | 623/6 |
| 4,880,426 | 11/1989 | Ting et al. | 623/6 |
| 4,888,013 | 12/1989 | Ting et al. | 623/6 |
| 4,888,014 | 12/1989 | Nguyen | 623/6 |
| 4,894,062 | 1/1990 | Knight et al. | 623/6 |
| 4,932,970 | 6/1990 | Portney | 623/6 |
| 4,938,767 | 7/1990 | Ting et al. | 623/6 |
| 4,957,505 | 9/1990 | McDonald | 606/107 |
| 4,959,070 | 9/1990 | McDonald | 606/107 |
| 4,978,354 | 12/1990 | Van Gent | 623/6 |
| 5,030,231 | 7/1991 | Portney | 623/6 |
| 5,044,743 | 9/1991 | Ting | 623/6 |

*Primary Examiner*—Randy C. Shay
*Attorney, Agent, or Firm*—William W. Haefliger

[57] ABSTRACT

A foldable plastic lens insertible into the eye lens zone from which a natural lens has been removed comprising the plastic lens having a light passing intermediate and bead-like optical portion, and two oppositely extending haptics; the lens also having two opposed peripheral segments characterized as light blocking; and the segments having substantially reduced thickness relative to the thickness or thicknesses of the main extent of the intermediate optical portion. Reinforcement strands are typically incorporated with the segments, and may assist in anchoring the haptics.

19 Claims, 6 Drawing Sheets

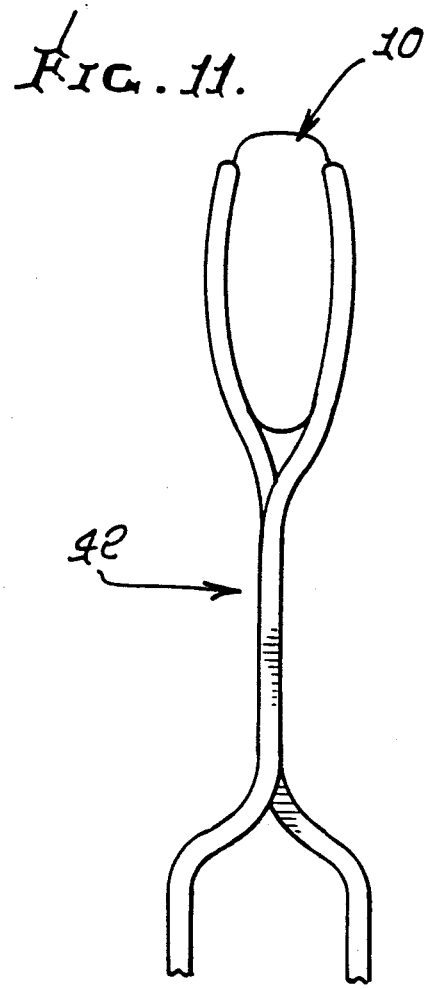
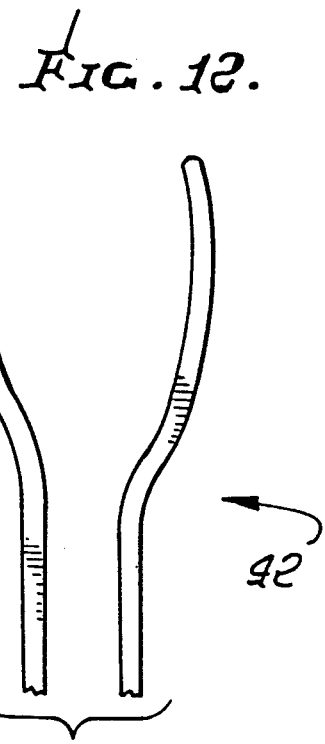
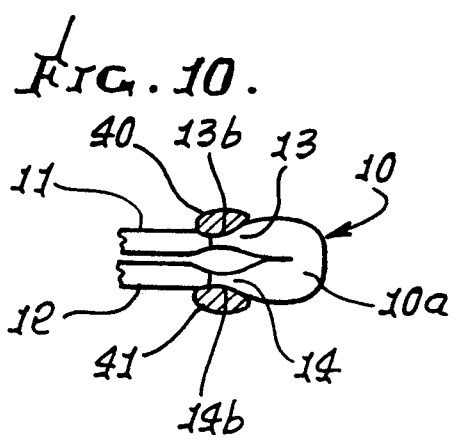
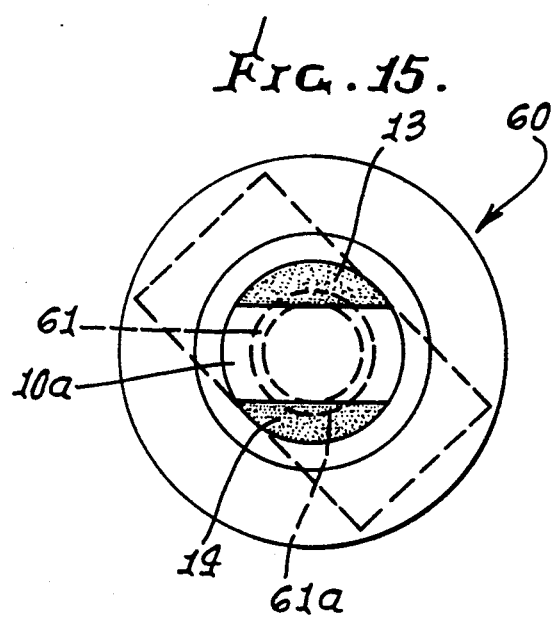

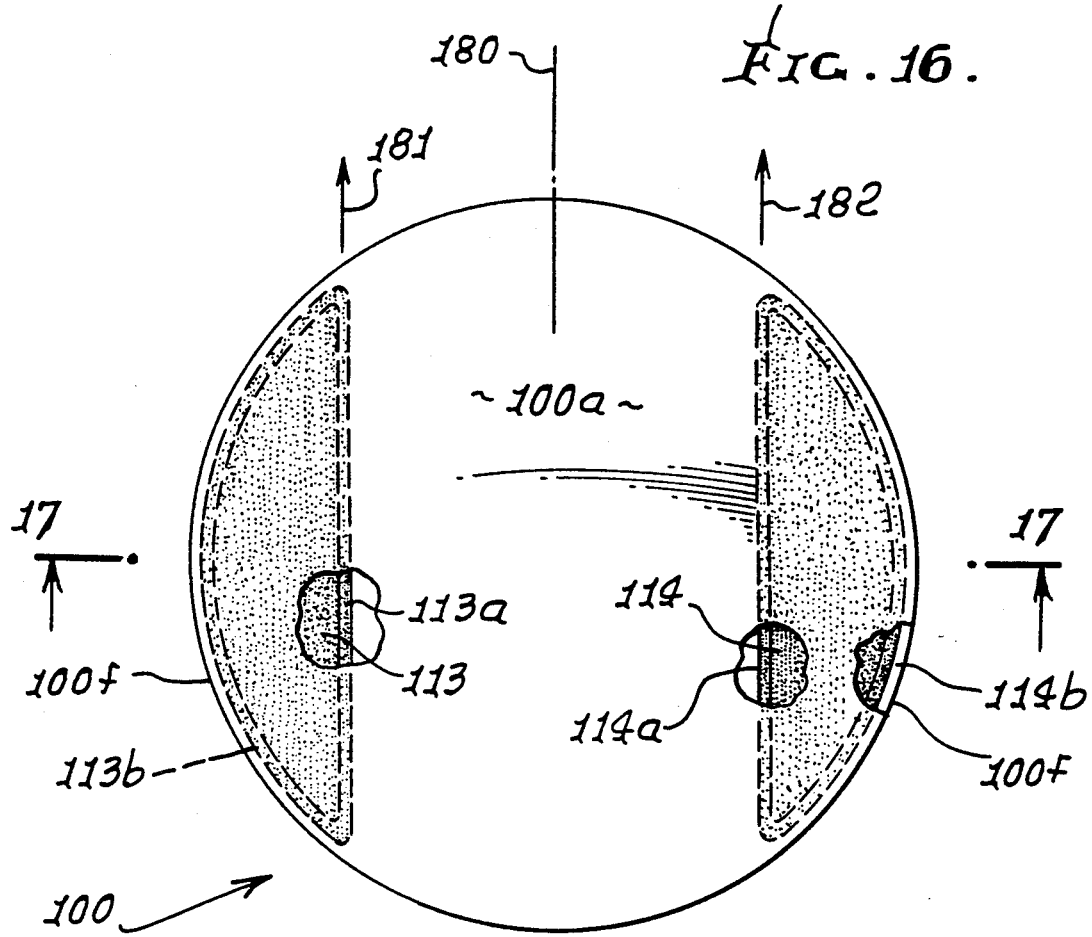
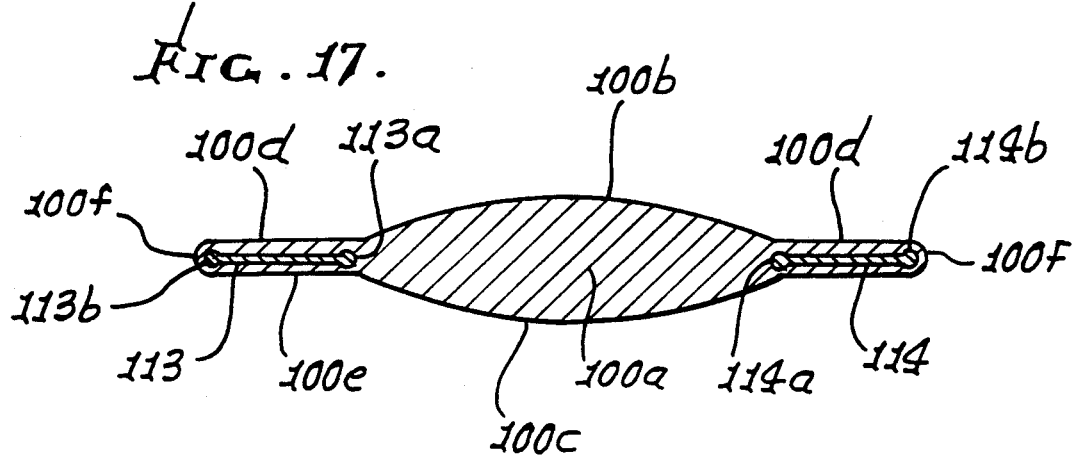

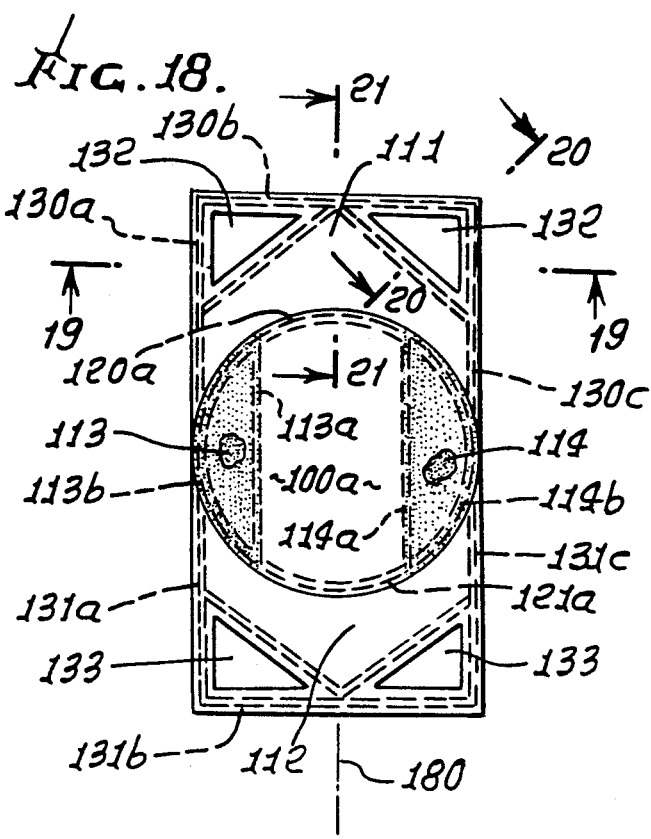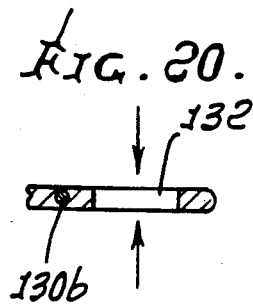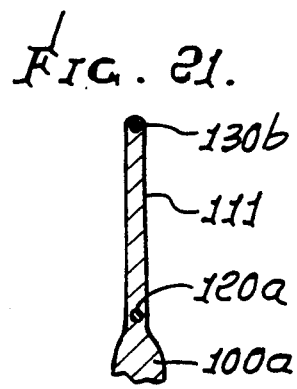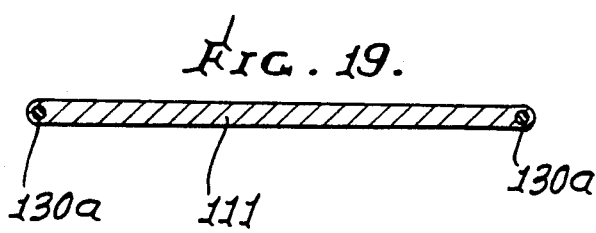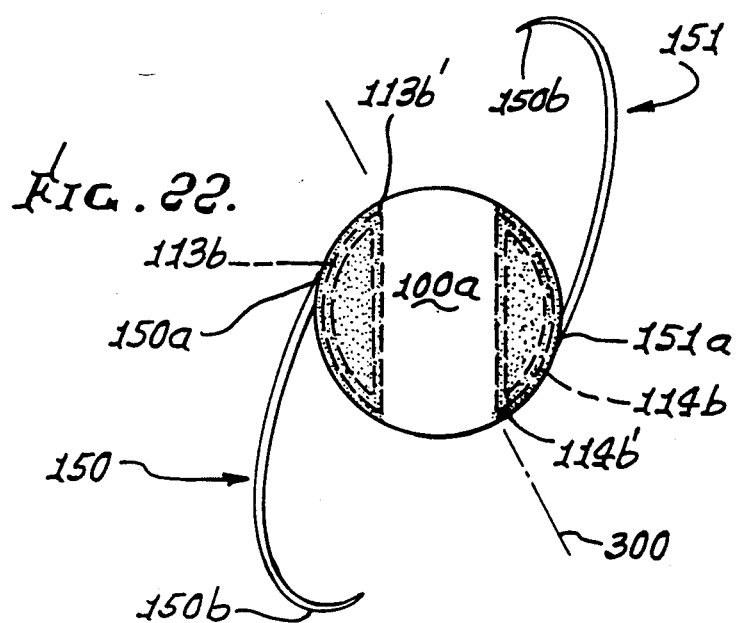

FOLDABLE PLASTIC OPTICAL LENS WITH REDUCED THICKNESS LIGHT BLOCKING SEGMENTS, AND ANCHORING MEANS

This application is a continuation-in-part of Ser. No. 791,002, filed Nov. 12, 1991.

BACKGROUND OF THE INVENTION

This invention relates generally to method and apparatus for insertion of a foldable lens or optic through a narrow width incision in the eye; and into the corneo-scleral limbus of the eye, more particularly it concerns formation and use of a foldable lens having light occluding, de-bulked portions or segments to facilitate such insertion.

Recent efforts to achieve clear vision by use of a lens implant have led to use of a hard plastic lens of narrowed width to be passed through an incision or wound (of about 7 mm length) in the eye surface. However, visual distortion can then result, because external light rays can then pass through the pupil extents not covered by the reduced dimension lens implant, during de-centering of the lens implant in the eye.

Visual distortion and "glare" become increasingly disabling with either enlargement of the pupil, or decentration of the lens implant, both of these being possible under extreme conditions. Decentration occurs when the lens implant is improperly placed in the eye, or adhesions draw the implant out of centered condition. Further, the pupil can be dilated excessively due to medication or stimulation such as created by fear or excitement, or in a dark environment.

There is, accordingly, need for a means to alleviate the problem of such visual distortion, as well as need for improvements in soft lenses that will avoid the visual distortion problem as well as aid insertion of such lenses, as through narrowed incisions. There is also need for a distortion alleviating provision of an opaque zone on the lens, especially when de-bulking of the optic is present, and especially under decentration conditions.

SUMMARY OF THE INVENTION

It is a major object of the invention to provide a special lens implant which overcomes the above problems, in a very simple manner. The invention contemplates use of a foldable soft lens having abruptly reduced bulk and thickness, at an opaque edge segment or segments, which may complete the lens fold cross-dimension (typically about 6 mm).

Basically, the foldable malleable lens (for example consisting of silicone) of the present invention incorporates at least one de-bulked or thinned peripheral segment and preferably two peripheral segments, which enable or facilitate folding, especially folding of haptics connected to the lens, such segments also characterized as occluded or darkened to prevent light ray passage. Such segments are positioned at locations such that the light passing extent of the lens has reduced width (as referred to above) between the segments, but can have normal width (up to 6 mm) along an axis parallel to the segments, the lens being foldable to pass through the narrow width incision in the eye. The reduced thickness segments typically also form pockets to receive and locate the forceps blades during lens folding, implantation, and unfolding in the eye, for better and more reliable control of these steps, as will be seen.

It is another object of the invention to provide an implantable folded lens that facilitates insertion through an incision in the eye, and which also enables reduction in lens size, through use of occluded lens segments, de-bulked in size. Basically, the lens of the invention is characterized as a) having a light passing intermediate and bead-like optical portion, and two oppositely extending haptics, b) the lens also having two opposed peripheral segments characterized as light blocking, c) said segments having substantially reduced thickness relative to the thickness or thicknesses of the main extent of said intermediate optical portion.

As will be seen the two segments are typically of substantially equal size and shape, and may extend adjacent the intermediate optical portion along a substantially linear border. Further, the lens has an optical axis, and there being a flat plane containing said optical axis which bisects one of the segments and also bisects the other of the segments.

It is another object to provide a lens as referred to wherein the haptics are in the form of flat, foldable and flexible plastic tabs that extend directionally longitudinally oppositely, the segments each elongated in skewed relation to said haptics longitudinal direction. The lens is typically foldable along a fold axis parallel to the two segments, to bring the flexible segments into superposition for insertion through a very small width eye incision, and into the corneo-scleral limbus. The two segments may abruptly taper away from the intermediate optical portion of the lens, and the lens may be gripped by forceps at the superposed reduced thickness segments to enhance grippability of the folded lens, as during its insertion into the eye along with haptics attached to the lens, to ensure gripping of the folded lens during its controlled rotary positioning in the eye, and to enable controlled release and expansion of the folded lens, i.e. prevent "explosive expansion".

The basic method of the invention includes the steps
  i) folding the lens to superimpose said segments,
  ii) causing the blades to grip the folded lens at or proximate said superposed segments, and
  iii) inserting the folded lens into the eye via the incision.

As noted, the method may advantageously include engaging the blades against the reduced thickness segments during progressive folding of the lens, and during progressive unfolding of the lens, in the eye.

These and other objects and advantages of the invention, as well as the details of an illustrative embodiment, will be more fully understood from the following specification and drawings, in which:

DRAWING DESCRIPTION

Figure 13:
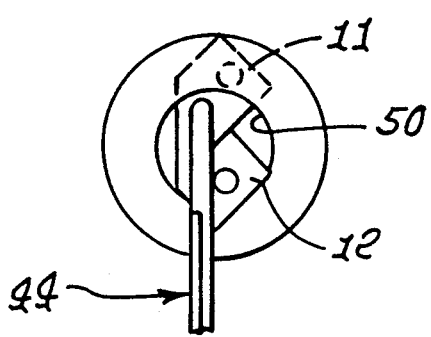
Figure 14:
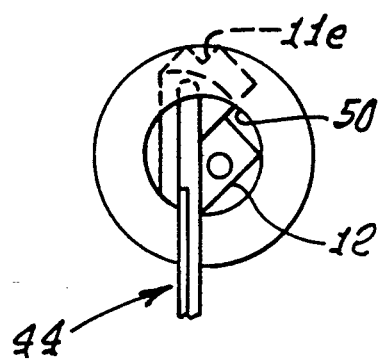
Figure 9A:
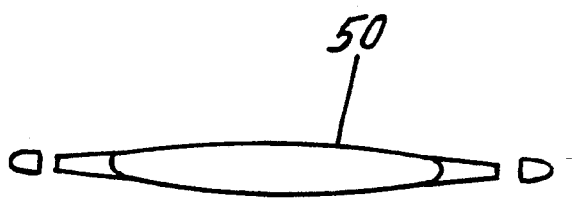
Figure 9B:
Figure 9C:
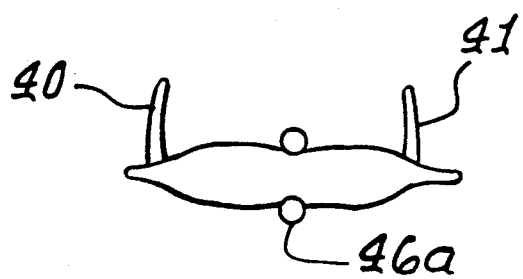
Figure 9D:
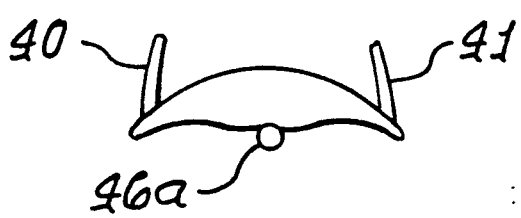
Figure 9E:
Figure 9:
Figure 9G:
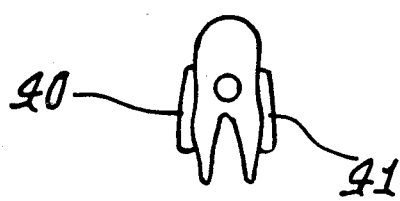

FIGS. 9 (a)-(g) are views showing progressive folding of the lens;

FIG. 10 is an edge view of a folded lens with folding forceps received in pockets formed by light blocking peripheral segments of reduced "de-bulked" thickness;

FIG. 11 is an enlarged view showing forceps blades holding a lens in folded condition;

FIG. 12 shows the FIG. 11 forceps blades in released condition;

FIGS. 13 and 14 show folded lens insertion into the eye;

FIG. 15 shows the released lens and light blocking segments in the eye;

FIG. 16 is a frontal view of a further modified plastic lens;

FIG. 17 is a section taken on lines 17—17 of FIG. 16;

FIG. 18 is a frontal view of a lens as in FIGS. 16 and 17, with attached solid haptics anchored to the lens;

FIG. 19 is an enlarged section taken on lines 19—19 of FIG. 18;

FIG. 20 is an enlarged section taken on lines 20—20 of FIG. 18;

FIG. 21 is an enlarged section taken on lines 21—21 of FIG. 18; and

FIG. 22 is a frontal view of a lens as in FIGS. 16 and 17, but with spiral haptics anchored to the lens.

DETAILED DESCRIPTION

Figure 1:
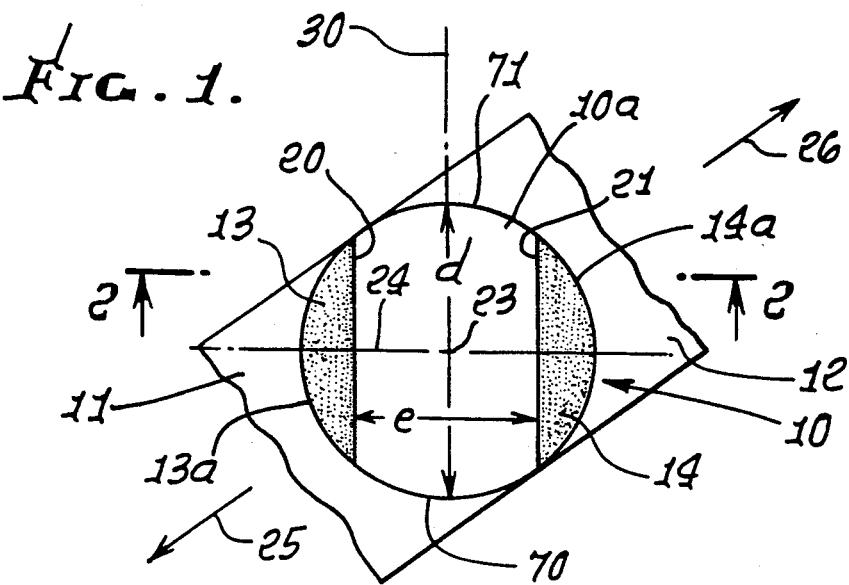
FIG. 1 is a front view of a modified plastic lens incorporating the invention.
Figure 2:
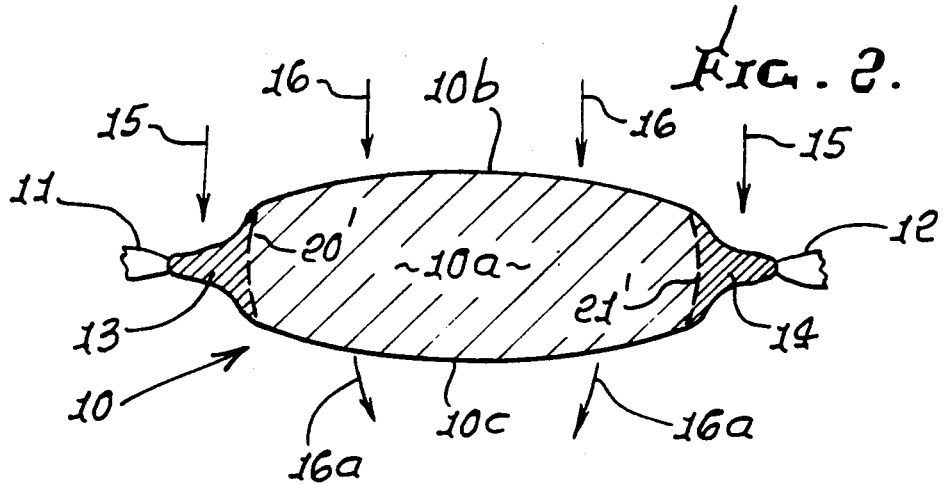
FIG. 2 is an enlarged section taken on lines 2—2 of FIG. 1.

In FIGS. 1 and 2, a plastic, foldable lens 10 is shown, sized for resiliently yieldable folding and insertion into the eye lens zone from which a natural but cataractous lens has been removed. One highly advantageous technique for such insertion is disclosed in U.S. Pat. No. 4,813,957, other techniques being usable. The bead-like lens, which may consist of silicone or equivalent material, has a light passing intermediate zone 10a between outwardly convex lens surfaces 10b and 10c. Attached to the lens generally circular periphery are two oppositely extending, solid haptics 11 and 12. Loop type haptics may alternatively be employed. See the publication entitled "Simultaneously Endocapsular Implantation of Haptics and Optic Segment Using Cross-Action Folding Forceps", by Henry H. McDonald, M.D.

In accordance with one aspect of the invention, the lens also has two opposed peripheral segments 13 and 14 which are characterized as light blocking. They may be internally darkened, or cloudy, or occluded, or the surfaces of the segments may be treated so as to be irregular, or occluded or darkened, to achieve light blocking effect. See light rays 15 in FIG. 2, blocked by 13 and 14, whereas light rays 16 incident on the lens light passing and refracting intermediate portion 10a are not blocked, and pass from the lens at 16a. Further, the segments 13 and 14 have substantially reduced thickness (de-bulking) over their major extents, relative to the thickness of 10a over its major extent. Note also that the two segments typically have substantially equal size and shape, and they extend adjacent the intermediate optics portion 10a along substantially linear and parallel borders 20 and 21 as seen in FIG. 1. Such borders appear as planes 20' and 21' in FIG. 2. Also, the segments have generally convex outer edges 13a and 14a. Typical dimensions are as follows:

$d \approx 6$ mm $e \approx 3$ to 4 mm where "d" is the diameter of the intermediate portion 10a, and "e" is the spacing between the segments, as seen in FIG. 1.

As also seen in FIG. 1, the lens has an optical axis 23, and there is a flat plane 24 containing that axis 23 that bisects both of the segments. That plane extends generally normal to the parallel, linear borders 20 and 21. Plane 24 also bisects the lens intermediate portion 10a. Each of the segments 13 and 14 has thickness which tapers or reduces, directionally away from the intermediate portion 10a, as is seen in FIG. 2. Thus, the segments are de-bulked relative to intermediate portion 10a.

The haptics 11 and 12 are in the form of flat, foldable and flexible plastic tabs that extend directionally longitudinally oppositely—see arrows 25 and 26 in FIG. 1, whereby each segment 13 and 14 is elongated in skewed relation to the longitudinal direction of tab elongation. As will appear, these relationships facilitate superposition of the reduced thickness segments 13 and 14 during lens and tab folding, to minimize the overall width of the folded assembly for insertion through an incision in the corneo-scleral limbus. Also, as is clear from FIG. 2, the haptics have secure attachment to the lens at lens peripheral regions 70 and 71, offset from the thin segments 13 and 14 which offer less secure attachment of the haptics to the lens.

Figure 3:
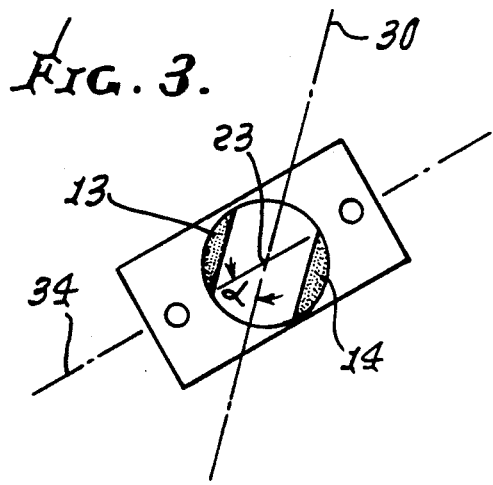
FIG. 3 is a front view of a lens as in FIG. 1, together with attached solid haptics.
Figure 4:
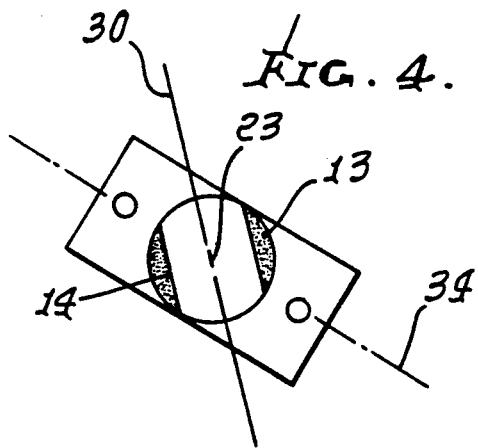
FIG. 4 is a rear view of the FIG. 3 lens and haptics.

The lens also defines a fold axis 30 that bisects the intermediate optical portion 10a. See FIGS. 1, 3, 4, 5 and 6, the axis 30 passing through axis 23. Segments 13 and 14 are elongated in generally parallel relation to that fold axis 30, which extends crosswise of the longitudinal axis 34 of haptic elongation, at an acute angle $\alpha$, as seen in FIG. 3. Axis 34 also passes through axis 23.

Figure 5:
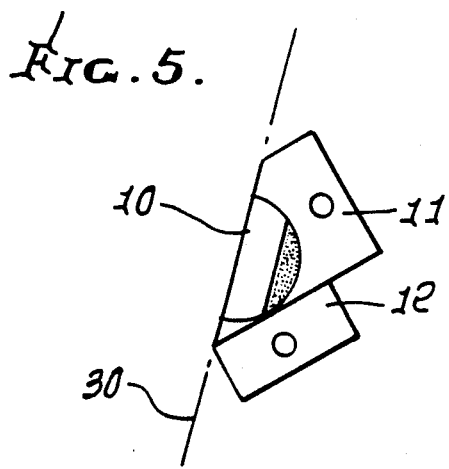
FIG. 5 is a front view of the FIG. 3 lens and haptics in folded condition.
Figure 6:
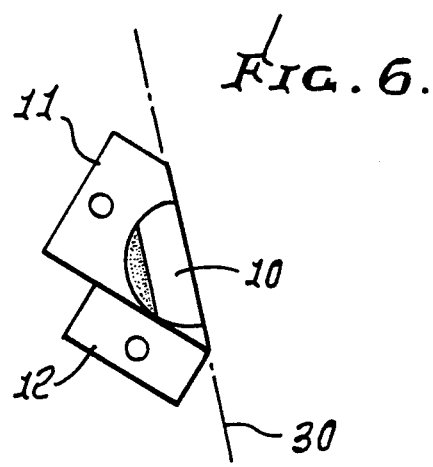
FIG. 6 is a rear view of the FIG. 5 folded lens and haptics.

FIGS. 5 and 6 show the resiliently foldable lens as having been folded along axis 30 to bring the de-bulked two segments 13 and 14 into superposition, i.e. maintains the segments in parallel, closely spaced relation. De-bulking of the lens segments 13 and 14 accordingly allows for forceps gripping of the lens at pockets formed by the outwardly facing tapered surfaces 13b and 14b of the segments, as seen in FIG. 10, significantly enhancing grippability of the folded lens by the forceps, and resultant assurance against forceps displacement relative to the lens as during folding, maneuvered insertion of the lens and haptics through a narrow width wound (for example about 3 mm) in the eye, as referred to, rotation of the folded lens in the eye to position the haptics, and during lens release to control said release and prevent lens "explosive" unfolding. See the forceps blades 40 and 41 in FIG. 10, received in the pockets shown.

Figure 7:
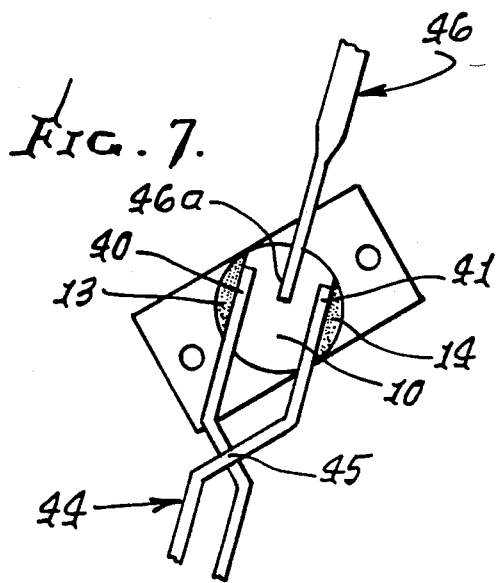
FIG. 7 is a front view showing use of holding and folding forceps during lens folding.
Figure 8:
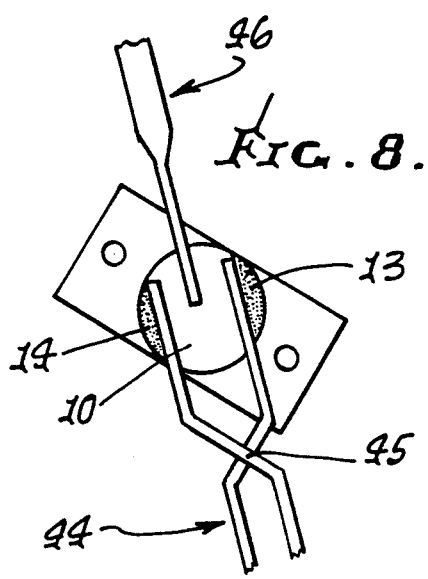
FIG. 8 is a rear view of the FIG. 7 forceps and lens, during folding.

Cross-over type forceps may be employed for lens insertion into the eye "bag", as described in U.S. Pat. No. 4,813,957. FIGS. 11 and 12 show another type forceps 42 holding a lens 10, FIG. 12 showing the forceps controllably expanded to release the lens. FIG. 7 shows the use of cross-over forceps 44 (see cross-over point 45), with blades 40 and 41 extending in parallel relation, and placed adjacent segments 13 and 14. Blade an of a holding forceps 46 projects oppositely as shown, as along the fold axis 30, to hold or position the lens 10 during folding. The forceps blades 40 and 41 may be pressed downwardly to fold the lens about axis 30. See FIG. 9, steps (c) through (g), showing progressive lens folding as blades 40 and 41 are pressed down relative to blade 46. Blades 40 and 41 remain in the pockets formed by segment surfaces 13b and 14b (see FIG. 10) during such folding, the blades also being closed partially together during lens folding. Blade 46a is axially withdrawn as at or near step 9(f). FIG. 9(a) shows a wound or incision 50 in the eye, and FIG. 9(b) shows a lens 10a, of FIGS. 1 and 2 type, haptics not being shown.

FIGS. 13 and 14 show insertion of the folded lens and haptics into an eye lens zone, via the narrow wound, and via the opening 50 of the anterior capsulatory 50. In FIG. 14 the folded lens and haptics are inserted more deeply than in FIG. 13, and the corner 11e of the forward haptic 11, becomes folded back, as shown.

FIG. 15 shows the unfolded lens and haptics in the eye 60. Segments 13 and 14 are positioned (by lens rotation) to extend generally horizontally, above and below the lens intermediate portion 10a; i.e. the portion 10a is elongated left and right to pass maximum left and right light through the lens to the eye retina, i.e. the effective width of the lens is not reduced, so as not to inhibit left and right vision. The occluded de-bulked segments 13 and 14 block light passage (light that would otherwise be distorted due to thinning or de-bulking at 13 and 14); but any inhibition of up-down vision is of lesser importance and such up-down vision is normally inhibited anyway by squinting of eyelids. The normal pupil appears at 61, and the expanded pupil at 61a.

Looping haptics may be employed in place of the tab-like haptics described.

In FIG. 10, not that the total thickness of the superposed two blades and two segments is substantially the same or less than the total thickness of the two halves of the folded intermediate optical portion of the lens.

In FIGS. 16 and 17, the bead-like silicone lens 100 having surface 110a is like lens 10 described above, and is foldable at axis 180, into two halves. It has a light passing intermediate zone 100a between outwardly convex lens surfaces 100b and 100c.

The lens also has two opposed peripheral segments 113 and 114 characterized as light blocking. The segments are anchored to the lens intermediate portion, and anchoring means may take one or both of two forms, as shown. In FIG. 17 the segments comprise thin webs embedded or encapsulated in lens plastic material, to anchor them to the lens intermediate portion, in the positions shown. See de-bulked lens material films 100d and 100e covering the opposite sides of the web-like segments, and joined at 100f at the curved outer peripheries of the segments, for further anchoring the segments. Also, and as another means of anchoring the segments, flexible, wire-like strands 113a and 114a are molded integrally with the segments, at their inner edges, and extend in parallel linear directions 180 and 181, along opposite borders of the lens intermediate portion 100a, and at the inner peripheries of the web-like segments as shown. Each such anchoring means has thickness substantially less than thickness of said main extent of said lens intermediate portion.

The foldable strands 113a and 114a may be integrally molded with the segments, and have diameters larger than the thickness of the main extents of the segments.

The anchoring means may also extend along the outer peripheries of the segments. See reinforcement strands 113b and 114b which extend arcuately near the outer peripheries 110f. Strands 113b and 114b as well as reinforcement strands 113a and 114b may be integrally molded with thin segments 113 and 114, as from plastic material such as polypropylene, and the latter may be colored so as to be opaque, i.e. blocking to light transmission. The segments and strands are flexible and foldable. Segments 113 and 114 together with the lens material layers 110d and 110e have substantially reduced thickness (de-bulking) over their major extents, relative to the thickness of 110a over its major extent, and may have dimensions about the same as segments 13 and 14, described above.

Referring now to FIG. 18, the construction is the same as in FIGS. 16 and 17, but haptics and additional reinforcement strands are provided. Note strands 120a and 121a extending along the curved peripheral sections of the lens intermediate region 100a, and incorporated in the lens material. Such strands may be formed as continuations of strands 114a, and may intersect strands 113a at their ends.

In FIGS. 18-21 like haptics 111 and 112 are in the form of flat, foldable and flexible plastic tube, like those described above at 11 and 12. Lengthwise folding of the lens along "bisecting" axis 180 also results in "bisecting" folding of the two haptics. Folding can also be carried out as in FIGS. 1-15, or along an axis 181 extending proximate ends of the segments as seen in FIG. 16. The reinforcement strands 120a and 121a also act to assist anchoring of the two haptics 111 and 112 to the lens intermediate portion 100a. See FIG. 21. Reinforcement strands may also be molded into (encapsulated in) the haptics, near their outer edges, as indicated at 130a-130c, and 131a-131c, The haptics may consist of elastomide the same silicon material as the lenses intermediate portion 100a, whereas the strands 130 and 131 may consist of the same material as segments 113 and 114, or associated strands as described. Corner portions of the haptics may define one or more through openings, seen at 132 and 133, to allow growth of eye tissue through such openings, to assist in positioning the haptics in the eye, as described above in FIG. 15. Segments 113 and 114 may be obliquely angled relative to axis 180, as in FIG. 1.

FIG. 22 shows a lens like that of FIGS. 16 and 17 but having two lens positioning haptics 150 and 151 comprising narrow (plastic, such as polypropylene) fingers with inner end portions 150a and 151a anchored by the anchor strands 113b and 114b. Such anchoring may be by suitable attachment to 113b and 114b, near cusps 113b' and 114b'. Portions 150a extend sidewise generally parallel to 113b and 114b. Outer end portions of the two haptics curl at 150b and 151b, as conventional. They may consist of molded plastic material. Their positioning enables folding overlay of the haptics, for implantation, if the fold is along axis 300.

Referring back to FIG. 18, the strands 113a, 113b, 114a, 114b, 130a-c, and 131a-c may be preliminarily formed or molded as a "skeleton", to provide reinforcement when the silicone lens is molded to integrate and encapsulate the "skeleton" or framework, with the haptics, forming the complete article. Strands 120a and 121a may be included in the skeleton.

I claim:
1. A foldable lens insertible into the eye lens zone from which a natural lens has been removed, comprising
   a) the lens having a light passing intermediate optical portion, consisting of plastic,
   b) the lens also having opposed peripheral segments characterized as substantially light blocking,
   c) and anchoring means for anchoring said segments to the intermediate optical portion, d) said anchoring means extending along outer peripheries of said segments.

2. The lens of claim 1 wherein said anchoring means has at least one of the following forms:
   i) material attached to the intermediate optical portion in which the segments are embedded,
   ii) at least one elongated strand integral with the segments and embedded in an outer edge portion of said intermediate optical portion.

3. The lens of claim 2 wherein the anchoring means has thickness substantially less than the thickness of said lens intermediate optical portion.

4. The lens of claim 1 wherein said lens intermediate optical portion has an edge and said anchoring means also extends along said edge of said lens intermediate optical portion and in spaced relation to said segments.

5. The lens of claim 1 wherein the foldable lens also has two generally oppositely extending haptics anchored to said lens intermediate optical portion via said anchoring means.

6. The lens of claim 5 wherein said haptics are anchored to said lens intermediate optical portion proximate said segments.

7. The lens of claim 6 wherein said segments are of substantially equal size and shape.

8. The lens of claim 6 wherein each of said segments extends adjacent said lens intermediate optical portion along a substantially linear border.

9. The lens of claim 6 wherein said segments have substantially reduced thickness relative to the thickness of said intermediate optical portion.

10. The lens of claim 5 wherein said haptics comprise flat tabs projecting oppositely.

11. The lens of claim 10 including reinforcement strands extending in said haptics, proximate edges thereof.

12. The lens of claim 10 wherein said lens includes reinforcement strands anchoring the haptics to said lens intermediate optical portion.

13. The lens of claim 12 wherein said strands are foldable, and extend arcuately, in spaced relation to said segments.

14. The lens of claim 10 including openings through said flat tab haptics to allow growth of eye tissue therethrough.

15. The lens of claim 5 wherein said haptics comprise narrow fingers having first end portions anchored by said anchoring means, and second end portions that curl in spaced relation to the lens intermediate optical portion.

16. The lens of claim 1 wherein said anchoring means comprises at least one flexible strand.

17. The lens of claim 1 wherein said segments have substantially reduced thickness relative to the thickness of said intermediate optical portion.

18. The lens of claim 1 wherein said intermediate optical portion is light transparent, and said segments are opaque.

19. The lens of claim 1 wherein said segments each include a core layer integral with said anchoring means, and clear plastic layers at opposite sides of said core layer.

* * * * *